US00PP30465P3

(12) United States Plant Patent
Wells

(10) Patent No.: US PP30,465 P3
(45) Date of Patent: Apr. 30, 2019

(54) ***SCHEFFLERA* PLANT NAMED 'MONHINSCHF'**

(50) Latin Name: *Schefflera taiwaniana*
Varietal Denomination: Monhinschf

(71) Applicant: Richard Wells, Dayton, OR (US)

(72) Inventor: Richard Wells, Dayton, OR (US)

(73) Assignee: Monrovia Nursery Company, Azusa, CA (US)

( * ) Notice: Subject to any disclaimer, the term of this patent is extended or adjusted under 35 U.S.C. 154(b) by 0 days.

(21) Appl. No.: 15/731,675

(22) Filed: Jul. 13, 2017

(65) Prior Publication Data

US 2019/0021204 P1 Jan. 17, 2019

(51) Int. Cl.
*A01H 5/12* (2018.01)
*A01H 6/00* (2018.01)

(52) U.S. Cl.
USPC ..... Plt./377
CPC ..... *A01H 6/00* (2018.05); *A01H 5/12* (2013.01)

(58) Field of Classification Search
USPC ..... Plt./377
See application file for complete search history.

*Primary Examiner* — Keith O. Robinson
(74) *Attorney, Agent, or Firm* — Cassandra Bright

(57) ABSTRACT

A new and distinct *Schefflera* cultivar named 'Monhinschf' is disclosed, characterized by bright yellow-green petioles on bushy, vigorous plants. 'Monhinschf' grows quickly, propagates easily and tolerates cold temperatures. The new variety is a *Schefflera taiwaniana*, normally produced as an outdoor ornamental garden or container plant.

1 Drawing Sheet

Latin name of the genus and species: *Schefflera taiwaniana.*

Variety denomination: 'Monhinschf'.

BACKGROUND OF THE INVENTION

The new *Schefflera* cultivar is a product of a breeding program under the direction of the inventor, Rick Wells, at a commercial nursery in Dayton, Oreg. The new variety was selected among a planting of seedlings of *Schefflera taiwaniana.*

Seed was bulk collect from several plants of an unpatented, unnamed proprietary variety of *Schefflera taiwaniana*. The new variety was selected among a planting of seedlings resulting from the bulk collected seed in May 2011.

First asexual reproduction of the new cultivar 'Monhinschf' was performed by tissue culture at a commercial laboratory in Dayton, Oreg. in May of 2011. Multiple generations and sub-divisions have been produced, and have shown that the unique features of this cultivar are stable and reproduced true to type in successive generations.

SUMMARY OF THE INVENTION

The cultivar 'Monhinschf' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Monhinschf'. These characteristics in combination distinguish 'Monhinschf' as a new and distinct *Schefflera* cultivar:

1. Superior branching.
2. Easier to propagate than typical for *Schefflera taiwaniana.*
3. Faster growth.
4. Better resistance to cold than typical for *Schefflera taiwaniana*
5. Bright yellow-green petioles.

PARENT COMPARISON

Plants of the new cultivar 'Monhinschf' are comparable to the parent *Schefflera taiwaniana* grown by the inventor. Plants of the new variety are similar in most horticultural characteristics to the parent variety, however, the new variety 'Monhinschf' differs in the following:

1. Plants of the new variety have better branching characteristics than the parent.
2. Plants of the new variety have yellow-green petioles, compared to dull green petioles, of the parent variety.
3. Plants of the new variety are more vigorous and grow faster.
4. Plants of the new variety propagate more easily.

COMMERCIAL COMPARISON

Plants of the new cultivar 'Monhinschf' are comparable to the variety *Schefflera taiwaniana* 'Yuan Shan', unpatented. The two *Schefflera* varieties are similar in most horticultural characteristics however, the new variety 'Monhinschf' differs having bright yellow-green petioles, whereas petioles of this comparator are green. Additionally plants of 'Monhinschf' are faster growing and easier to propagate than plants of 'Yuan Shan'. Plants of 'Monhinschf' also branch better than plants of this comparator.

BRIEF DESCRIPTION OF THE PHOTOGRAPH

FIG. 1: Illustrates in full color a plant of 'Monhinschf' in a 5 gallon pot, approximately 2 years old.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Monhinschf' plants grown in a polyhouse in Dayton, Oreg., USA. Temperatures ranged from about 5° C. to 15° C. at night and about 15° C. to 28° C. during the day. No artificial light, photoperiodic treatments were given to the plants. Measurements and numerical values represent averages of typical plant types.

Botanical classification: *Schefflera taiwaniana* 'Monhinschf'.

PROPAGATION

Time to initiate roots: About 30 to 45 days at approximately 22° C.

Root description: Woody, colored near RHS Grey-Brown 199A.

PLANT

Age of the plant described: Approximately 35 weeks.

Growth habit: Upright, outwardly spreading. Semi-temperate bushy evergreen small tree or shrub.

Pot size of plant described: 2 gallon.

Height: 55 cm.

Plant spread: 85 cm.

Growth rate: Vigorous.

Branching characteristics: Two main stems, each breaking into 2 to 4 lateral branches, producing an abundance of foliage with long petioles.

Length of stem: 15 to 22 cm.

Diameter of stem: 1.5 to 2.0 cm.

Characteristics of stem:

- *Form*.—Round.
- *Color*.—Near RHS Greyed-Brown 199C. Upper Stem (new growth) near Yellow Green 144A.
- *Texture*.—Glabrous. Oldest part of stem is rough with a somewhat woody texture. Irregularly occurring lenticels, moderate to sparse. Lenticels round to broad oblong, approximately 3 to 4 mm wide and 5 to 6 mm long. Lenticels colored near Grey-Brown N199B.
- *Strength*.—Very strong.

Internode length: 1.0 cm to 2.0 cm.

FOLIAGE

Leaf:

- *Arrangement*.—Spiral.
- *Quantity*.—Abundant, approximately 30 palmately compound leaves, composed of 6 to 9 leaflets. Most commonly 8 leaflets.

Leaf size:

- *Compound leaf*.—Leaflets arranged to form a nearly perfect circular shape.
- *Average diameter*.—20 to 25 cm.
- *Average length*.—20 to 25 cm.

Leaflets:

- *Average length*.—10 to 15 cm, including petiole. Smallest leaflet 10 cm, longest 15 cm.
- *Average width*.—2.2 to 2.7 cm.
- *Shape of blade*.—Elliptic.
- *Apex*.—Acute to almost acuminate.
- *Base*.—Attenuate.
- *Margin*.—Entire.
- *Texture of top surface*.—Glabrous.
- *Texture of lower surface*.—Glabrous.
- *Appearance of top surface*.—Matte.
- *Appearance of bottom surface*.—Matte.
- *Aspect*.—Flat to somewhat down-curved.
- *Color*.—Young foliage upper side: Near RHS Green 137A. Young foliage under side: Near RHS Green 138B. Mature foliage upper side: Near RHS Green 137A. Mature foliage under side: Near RHS Green 138C.
- *Fragrance*.—None observed.
- *Orientation*.—About 75 to 90 degrees (horizontal) from center of plant.
- *Venation*.—Type: Pinnate. Venation color upper side: Near RHS Green 143B. Venation color under side: Near RHS Green 143A.
- *Petiole*.—Length: Average range 25 to 30 cm. Average length: 20 to 25 cm. Diameter: Average 6 mm at stem attachment, 3 mm at leaf attachment. Color: Near RHS Yellow-Green 144A. Texture: Glabrous. At stem attachment farinous, colored near Grey-Brown 199A.
- *Leaflet petiole*.—Length: 1.5 cm. Diameter: 3 mm. Color: Near RHS Yellow-Green 145A. Texture: Glabrous.

FLOWER

Not observed to date.

OTHER CHARACTERISTICS

Disease/pest resistance: Neither resistance nor susceptibility to pathogens and pests common to *Schefflera* have been observed.

Temperature tolerance: The new variety tolerates temperatures between 0 to 40° C.

What is claimed is:

1. A new and distinct cultivar of *Schefflera* plant named 'Monhinschf' as herein illustrated and described.

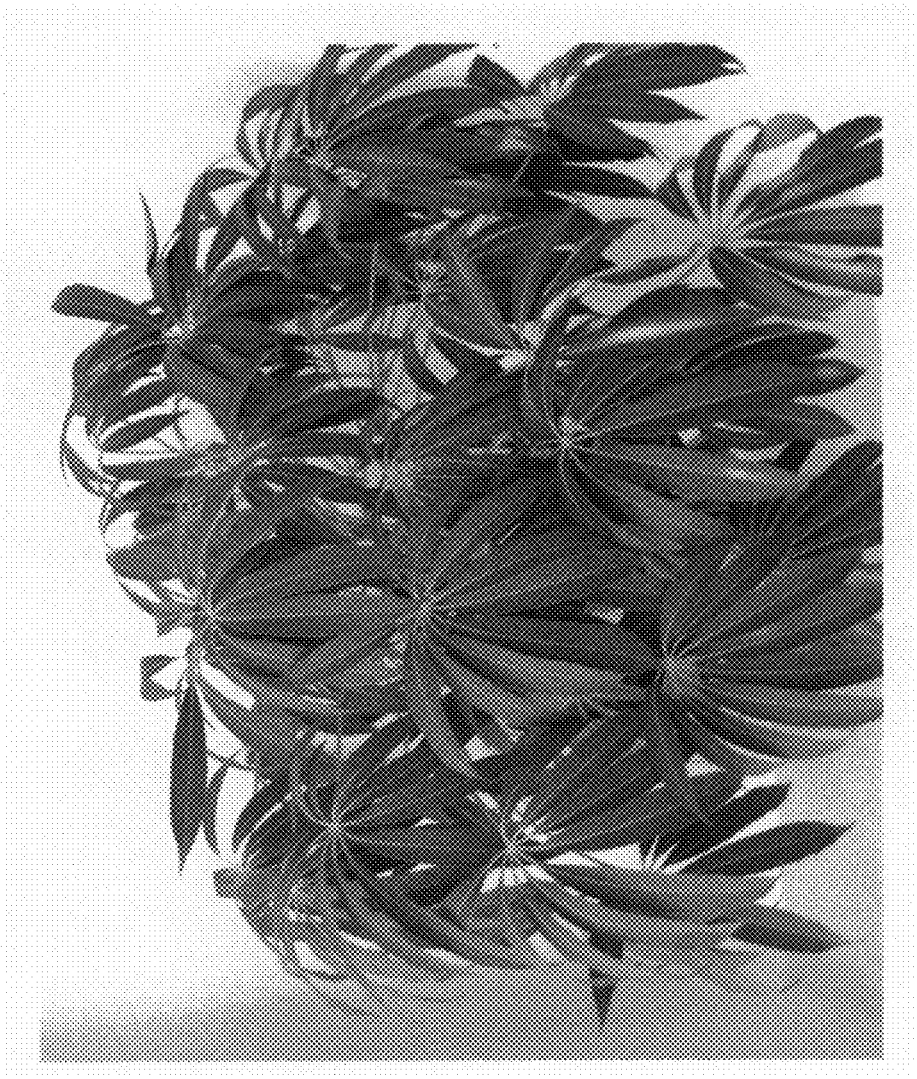

* * * * *